U
nited States Patent [19]

Ogawa et al.

[11] 4,303,409

[45] Dec. 1, 1981

[54] METHOD, COMPOSITION AND TEST STRIP FOR COLORIMETRIC ANALYSIS OF ASCORBIC ACID

[75] Inventors: Yasunao Ogawa, Ikeda; Kaoru Ishitobi, Yao, both of Japan

[73] Assignee: Shionogi & Co., Ltd., Osaka, Japan

[21] Appl. No.: 140,675

[22] Filed: Apr. 15, 1980

[30] Foreign Application Priority Data

Apr. 24, 1979 [JP] Japan .................................. 54-51278

[51] Int. Cl.$^3$ ...................... G01N 33/52; G01N 33/82
[52] U.S. Cl. .................................. 23/230 B; 23/904; 23/932; 252/408; 422/56
[58] Field of Search ...................... 23/230 B, 901, 904, 23/932; 422/56, 57; 252/408; 435/28

[56] References Cited

U.S. PATENT DOCUMENTS

| | | | |
|---|---|---|---|
| 3,104,209 | 9/1963 | Scott | 422/56 X |
| 3,266,868 | 8/1966 | Harvill | 23/932 X |
| 3,282,649 | 11/1966 | Bittner | 23/901 X |
| 3,411,887 | 11/1968 | Ku | 23/932 X |
| 3,954,412 | 5/1976 | Ogawa et al. | 422/56 |

*Primary Examiner*—Arnold Turk
*Attorney, Agent, or Firm*—Birch, Stewart, Kolasch & Birch

[57] ABSTRACT

A system composed of a complex of a chelating agent with a polyvalent metal ion in its higher valency, an indicator capable of reacting with said metal ion in its lower valency and a buffering agent is disclosed as a composition and a test strip useful for colorimetric analysis of ascorbic acid present in body fluid.

12 Claims, No Drawings

METHOD, COMPOSITION AND TEST STRIP FOR COLORIMETRIC ANALYSIS OF ASCORBIC ACID

BACKGROUND OF THE INVENTION

1. Field of the Invention

The present invention relates to a composition and a test strip for colorimetric analysis (detection and determination) of ascorbic acid present in an aqueous liquid, particularly, in body fluid.

The ascorbic acid (hereinafter, referred to as VC) is contained in foods, fodders and beverages, especially in enriched ones, and in nutritional supplement pills at relatively high concentrations. Thus, it is present in body tissues, blood and excrements at a correspondingly high concentration when they are ingested by or administered to humans or animals.

When detection or determination of another particular substance in the body fluid, especially urine or blood, is intended, there is a frequent possibility of creating an abnormal error in the measurement value of the other substance intended to be determined because of the high reducing ability of the coexistent VC which greatly affects the value.

For instance, when determination of the amount of glucose, galactose, cholesterol or uric acid in the body fluid is intended to be performed in accordance with a detection system composed of an enzyme, having an oxidizing activity specific to the particular substance, and peroxidase together with a redox chromogen, or when a detection of minute amounts of blood in urine is intended to be performed in accordance with a detection system of peroxidase and chromogen, a negative deviation from the actual amount may occur to an extent corresponding to the amount of the coexisting VC.

On the other hand, if determination of the amount of glucose, uric acid and the like is intended to be performed by a system based on a reduction method, a positive deviation from the actual value may occur to an extent corresponding to the amount of the coexistent VC.

2. Description of the Prior Art

Colorimetric titration analysis with indophenol is a heretofore widely known method for measuring VC in aqueous solutions. This method is, however, hardly regarded to be a practical method in clinical chemistry.

In clinical analysis, it is imperative to detect and determine the coexistent VC simultaneously with or, preferably, prior to the measurement of the previously mentioned other substances. The method for the latter measurement, which may be affected by the presence of VC, needs to be changed or modified according to the result of the determination of the coexistent VC.

Namely, it is desired to enable one to perform the detections and determinations of both substances in order to obtain accurate values thereof in an operation which is as simple as possible within a short period of time, thereby making the evaluation of the particular substance itself and its calibration with respect to the VC content possible at the same time.

One desired and simplified method for the measurement has been proposed in the specification of Japanese Patent Publication No. 712/78. This method is based on a principle that phosphorous molybdate can react with a substance having a reducing activity to form molybdenum blue (molybdenum oxide) and has been utilized as a known method for a quantitative determination of minute amount of inorganic phosphor. This method is, however, still unsatisfactory because the applicable range of VC concentration is limited only to 0–40 mg/dl and because of poor stability in the color development.

SUMMARY OF THE INVENTION

It is therefore a primary object of the present invention to provide a composition and a test strip for colorimetric analysis of VC in an aqueous liquid, particularly body fluid, in a simple operation, within a short period of time, for a wide range of concentrations and with sufficient accuracy.

It is another object of the present invention to provide a means for correcting or calibrating the determined value of a particular substance with respect to the concentration of the VC.

According to the present invention, there is provided a composition for colorimetric analysis of ascorbic acid, which comprises; a complex of a chelating agent with a polyvalent metal ion in its lower valency, an indicator capable of reacting with said metal ion in its lower valency and a buffer capable of maintaining the pH value of the composition to from 3 to 6.5.

In another aspect of the present invention, a test strip for colorimetric analysis of ascorbic acid is also provided, which comprises; a bibulous body retaining the complex of a chelating agent with a polyvalent metal ion in its higher valency, an indicator capable of reacting with said metal ion in its lower valency, a buffering agent, a dye for adjusting background color and a dispersing agent.

In a preferred mode of the present invention, the test strip may be placed parallel to a small piece of the bibulous body to detect the particular substance in the form of a stick, so that the value of the latter can be read and interpreted in comparison with that of the former to make correction or calibration easy.

DESCRIPTION OF THE PREFERRED EMBODIMENT

In a preferred embodiment of the present invention, the disclosed polyvalent metal ion in the complex may be exemplified as iron, copper, cobalt and nickel ions, and among these, iron and copper ions are particularly preferred. Salts of the metals in their oxidized state (higher valency) may be exemplified as ferric chloride, ferric ammonium oxalate, ferric citrate, ferric ammonium citrate, ferric ammonium nitrate, ferric bromide, ferric ammonium sulfate, cupric acetate and the like.

The chelating agents capable of forming complexes with the polyvalent metal ions may be exemplified as ethylenediaminetetraacetic acid (EDTA), trans-1,2-cyclohexanediamine-N,N,N',N'-tetraacetic acid (CyHDTA), diethylenetriamine-N,N,N',N'',N'''-pentaacetic acid (DTPA), triethylenetetramine-N,N,N',N'',N''', N''''-hexaacetic acid (TTHA) and alkali metal salts thereof.

The organic metal indicators in general may preferably be selected from organic reagents of N,N-coordination for colorimetric analysis of the metal ion. These can be exemplified as o-phenanthroline, 4,7-diphenyl-1,10-phenanthroline, 2,2'-bipyridine (α,α'-dipyridyl), cuproine, neocuproine, 2,2',2''-tripyridine and the like. Any other organic reagents, capable of giving a detectable radiation absorbing band with the polyvalent metal ion in its lower valency, may equally be employed.

If the absorption band is outside of the visible ray region, the determination may be performed according to an ultraviolet or infrared absorption measurement.

The bibulous body for use in the test strip for simple detecting operation may be exemplified as filter paper, cloth, non-woven fabric, felt, sintered porous body of glass or ceramic powder which may further contain particles of adsorbent customary for thin layer chromatography.

The salts of the metals in their oxidized state may preferably be present in the composition at a concentration ranging from 0.01 mol to 0.1 mol. A concentration ranging from 0.05 mol to 0.08 mol is the most preferred concentration.

The chelating agent is usually contained in the composition at a concentration more than one molar ratio to the metal ion. If the chelating agent is absent, the required reaction specificity for the VC is largely lowered with concomittant decrease in the stability against radiation.

A salt of an organic acid with a strong inorganic base may be used as the buffer in a concentration sufficient for accomplishing the buffering object. Although the reaction on which the present invention is based can be performed at a pH value of the composition or the test strip in its wet state ranging from 3 to 6.5, it is highly desirable to use a buffer capable of maintaining the pH to a value ranging from 4 to 6 in order to completely avoid the adverse effect of any other reducing substance, for instance, uric acid, cysteine, sulfites, salicylate, glutathione, creatine, creatinine and the like.

A dye for adjusting background color such as appropriate food dyes of yellow No. 4 or blue No. 1, or an appropriate copper salt may be employed in the test strip in accordance with the desired clarity and sensitivity in the detection.

Conventional dispersing agents such as polyvinylpyrrolidone (PVP), hydroxypropyl cellulose (HPC) and polyethylene glycol (PEG) may preferably be employed, particularly, when the composition is retained in a test strip in a dried state. It may also serve as a stabilizer for the other ingredients and for maintaining homogeniety of the developed color. PVP is the most preferred in its performance.

In the following description, the present invention will be illustrated in more detail by way of example.

EXAMPLE 1

Filter paper (Toyo: No. 53) is impregnated with the first solution below and dried in vacuo at 45° C. for 90 minutes. After being impregnated again with the second solution below, it is dried in vacuo at 45° C. for 30 minutes to obtain a bulk roll for the test strip.

1st solution:

| | |
|---|---|
| CyHTA | 2 g |
| Ferric chloride | 1.2 g |
| Sodium citrate | 5.5 g |
| Citric acid | 1.3 g |
| Distilled water | 57 ml |
| Food dye, blue No. 1 (0.25 w/v %) | 2.5 ml |

2nd solution:

| | |
|---|---|
| 2,2''-bipyridine | 0.4 g |
| PVP or HPC | 0.5 g |
| Ethanol | 10 ml |
| Cyclohexanone | 30 ml |

The bulk roll of paper, after being impregnated and dried, is stored in a dark room at a low temperature. A small piece of paper is attached at a tip end of a strip of plastic sheet to obtain a test stick.

Evaluation of this stick is performed by dipping it into urine specimens of an apparently healthy volunteer which are free from VC, to which VC at the below concentrations is added. The color development on the small piece is observed after 60 seconds to obtain the following results:

| VC concentration (mg/dl) | Color (H-V/C) |
|---|---|
| 0 | 5 BG-7/6 |
| 5 | 7.5 BG-7/3 |
| 10 | 10 BG-6/2 |
| 20 | 7.5 R-5/2 |
| 40 | 5 R-5/4 |
| 80 | 2.5 R-4/4 |

EXAMPLE 2

Color developments similar to those described in Example 1 are observed after a 30 second dipping, with a test strip obtained in by a process identical with that of Example 1 except that the first solution had the following formula.

1st solution:

| | |
|---|---|
| TTHA | 2 g |
| Ferric chloride | 1.1 g |
| Sodium citrate | 4 g |
| Citric acid | 0.2 g |
| Distilled water | 42 ml |
| Food dye blue No. 1 (0.25 w/v %) | 1.8 ml |

EXAMPLES 3, 4 AND 5

Color developments similar to those described in Example 1 are observed with strips after 15 seconds dipping. In these cases, however, the first solutions of the following formulae are employed for preparing paper pieces for sticks.

1st solution:

| | Example 3 | Example 4 | Example 5 |
|---|---|---|---|
| DTPA | 2 g | — | — |
| EDTA-2Na | — | 3.5 g | 3 g |
| Ferric chloride | 1.2 g | — | — |
| Ferric ammonium oxalate | — | 3 g | — |
| Ferric citrate or ferric ammonium citrate | — | — | 2 g |
| Sodium citrate | 5.5 g | 6 g | 5 g |
| Citric acid | 1.2 g | 6 g | — |
| Distilled water | 57 ml | 95 ml | 95 ml |
| Food dye blue No. 1 (0.25 w/v %) | 2.5 ml | 5 ml | 5 ml |

EXAMPLE 6, 7 AND 8

In a similar manner to that of Example 1, test sticks are prepared with the solutions of the following formulae:

1st solution:

|  | Example 6 | Example 7 | Example 8 |
| --- | --- | --- | --- |
| EDTA-2Na | 3 g | 3 g | 3 g |
| Ferric ammonium nitrate | 3 g | — | — |
| Ferric bromide | — | — | 2 g |
| Ferric chloride | — | 2 g | — |
| Sodium citrate | 6 g | 5.8 g | 11 g |
| Citric acid | 3 g | 3 g | 5 g |
| Distilled water | 95 ml | 95 ml | 95 ml |
| Food dye yellow No. 4 (1 w/v %) | 2 ml | 2 ml | 2 ml |

2nd solution, common to Examples 6, 7 and 8:

| | |
| --- | --- |
| 2,2''-bipyridine or o-phenanthroline (both gave substantially the same color development) | 0.2 g |
| PVP or HPC | 0.25 g |
| Ethanol | 20 ml |

Color development observed with the sticks, after the 15 seconds dipping under similar conditions as Example 1 are as follows:

| VC concentration (mg/dl) | Color (H-V/C) |
| --- | --- |
| 0 | 5 Y-9/6 |
| 5 | 10 YR-8/8 |
| 10 | 5 YR-7/8 |
| 20 | 2.5 YR-7/10 |
| 40 | 10 R-6/12 |

EXAMPLE 9

Test sticks are prepared in a manner identical to that described in Example 1, except for the first solution which has the formula below. Color development observed with these sticks after the 10 second dipping is described below.

1st solution:

| | |
| --- | --- |
| EDTA-2Na | 3 g |
| Ferric ammonium sulfate | 7.1 g |
| Sodium citrate | 6 g |
| Distilled water | 95 ml |
| Food dye blue No. 1 (0.25 w/v %) | 5 ml |

Color development:

| VC concentration (mg/dl) | Color (H-V/C) |
| --- | --- |
| 0 | 5 BG-7/6 |
| 5 | 7.5 BG-7/3 |
| 10 | 10 BG-6/2 |
| 20 | 7.5 BG-6/2 |
| 40 | 5 BG-5/4 |
| 80 | 2.5 BG-4/4 |

EXAMPLE 10

Test sticks are prepared in a manner identical to that described in Examples 6, 7 and 8 except for the first solution which has the formula below.

1st solution:

| | |
| --- | --- |
| EDTA-2Na | 4 g |
| Ferric chloride | 2 g |
| Sodium citrate | 6.3 g |
| Citric acid | 3 g |
| Cupric acetate (anhydride) | 0.5 g |
| Distilled water | 95 ml |

Color developments after the 15 second dipping observed with this test strip are summarized as follows:

| VC concentration (mg/dl) | Color (H-V/C) |
| --- | --- |
| 0 | 10 GY-8/3 |
| 0.5 | 10 Y-7/3 |
| 1 | 10 YR-7/3 |
| 2 | 10 YR-7/2 |
| 5 | 5 YR-7/3 |
| 10 | 10 R-6/4 |
| 20 | 7.5 R-6/6 |

EXAMPLE 11

A similar procedure to that described in Example 1 is followed in obtaining test sticks which include the solutions below, and in observing color developments which will be described subsequent to the formula.

1st solution:

| | |
| --- | --- |
| Cupric acetate (anhydrous) | 0.2 g |
| EDTA-2Na | 0.5 g |
| Distilled water | 20 ml |

2nd solution:

| | |
| --- | --- |
| 4,7-diphenyl-1,10-phenanthroline | 0.2 g |
| PVP or HPC | 0.4 g |
| Ethanol | 20 ml |

Color development 1 (after 15 second dipping in urine):

| VC concentration (mg/dl) | Color (H-V/C) |
| --- | --- |
| 0 | 5 BG-8/3 |
| 5 | 10 BY-7/3 |
| 10 | 5 GY-7/3 |
| 20 | 2.5 GY-7/3 |
| 40 | 7.5 GY-4/4 |

Color development 2 (after 30 second dipping in serum, wherein the serum samples are prepared with, Hyland, Q-PAK chemistry Control Serum I and the varying concentration of VC):

| VC concentration (mg/dl) | Color (H-V/C) |
| --- | --- |
| 0 | 7.5 GY-8/3 |
| 1 | 5 GY-7/4 |
| 4 | 5 YR-7/3 |
| 10 | 7.5 R-6/6 |

EXAMPLE 12

In a manner similar to that described in Example 1, except with the solutions of the following formulae, test sticks are prepared and their color developments substantially identical to those in Example 1 are observed after the 15 second dipping in urine samples.

1st solution:

| | |
|---|---|
| EDTA-2Na | 3 g |
| Ferric chloride | 2 g |
| Sodium citrate | 5.6 g |
| Citric acid | 3 g |
| Distilled water | 94 ml |
| Food dye blue No. 1 (0.25 w/v %) | 5 ml |

2nd solution:

| | |
|---|---|
| 2,2''-bipyridine | 0.4 g |
| PVP | 0.5 g |
| Cyclohexanon | 27.5 ml |
| Ethanol | 12.5 ml |

EXAMPLE 13

A similar procedure to that described in connection with Example 12 is followed except for the use of a first solution of the below formula which is particularly designed for the evaluation of the serum sample. Special considerations are given to the amount of the dye for adjusting background color and liquid property.

Color developments observed are described subsequent to the formula.

1st solution:

| | |
|---|---|
| EDTA-2Na | 3 g |
| Ferric chloride | 2 g |
| Sodium citrate | 10 g |
| Distilled water | 94 ml |
| Food dye blue No. 1 (0.25 w/v %) | 0.3 ml |

Color development (after 30 second dipping in serum):

| VC concentration (mg/dl) | Color (H-V/C) |
|---|---|
| 0 | 5 Y-8/4 |
| 0.5 | 10 YR-8/3 |
| 1 | 7.5 YR-8/3 |
| 2 | 5 YR-8/4 |
| 5 | 10 R-7/6 |
| 10 | 7.5 R-6/8 |

In an investigation directed to possible adverse influences caused by coexistence of other medicaments, it has been confirmed that no such effect results therefrom with sodium fluoride, potassium oxalate, glutathione (reduced form), creatine, creatinine or pyruvic acid up to a concentration of 100 mg/dl and with uric acid or vitamine E up to a concentration of 5 mg/dl.

An addition of cysteine in a concentration of 25 mg/dl, however, resulted in a color development which corresponds to that of VC at 0.5 mg/dl.

COMPARATIVE PREPARATION AND EXPERIMENT

A procedure similar to that described in Example 1 is followed with the first solution being of the formula below, said solution being free from a chelating agent in preparing and evaluating test strips.

1st solution:

| | |
|---|---|
| Ferric chloride | 1 g |
| Citric acid | 1 g |
| Sodium citrate | 3 g |
| Distilled water | 45 ml |
| Food dye blue No. 1 (0.25 w/v %) | 2.5 ml |

Color developments (after 15 minutes dipping in urine):

| VC concentration (mg/dl) | Color (H-V/C) |
|---|---|
| 0 | 5 G-6/4 |
| 5 | 7.5 GY-4/2 |
| 10 | 5 Y-5/1 |
| 20 | 10 R-4/2 |
| 40 | 7.5 R-3/4 |

The obtained test sticks are liable to fading with age and were unable to withstand even a short term storing. A color development due to salicilate salt is observed.

EXAMPLE 14

(quantitative determination by a solution system)

The first solution constituting the system is prepared by dissolving 0.2 g of ferric chloride and 0.3 g of EDTA-2Na in 0.3 M citrate buffer (pH, 5.5) to make 100 ml and the second solution is prepared by dissolving 0.5 g of 2,2'-bipyridine in water to make 100 ml; both solutions are stored in darkness.

In determining VC content, 5 ml of the first solution is combined with 2 ml of the second solution, and added thereto a urine sample (0.1 ml or 1.0 ml of diluted (1/10) urine) and 0.3 M citrate buffer (pH, 5.5) to make the final volume 10 ml. The reaction mixture was a dark room for 2 minutes or more before measurement at 520 nm.

The curve obtained with standard samples gave a complete linear relationship of:

$$Y = 0.097X - 0.0014$$

wherein, X represents VC concentration in mg/dl and Y represents optical density at 520 nm., up to the VC concentration of 110 mg/dl.

The coefficient of variance (cv) of reproducibility in quantitative determination is under 1%.

Adverse influences caused by the other substances present in the sample expressed in the recovery rate, i.e., the specificity of this solution system for VC are summarized in the table below.

TABLE

| | Concentration of VC (mg/dl) | | | |
|---|---|---|---|---|
| | 5 | | 20 | |
| Other substances: (mg/dl) | Measured | Recovery (%) | Measured | Recovery (%) |
| 0 | 5.0 | 100.0 | 20.0 | 100.0 |
| p-Aminobenzoic Acid 100 | 5.0 | 100.0 | 20.0 | 100.0 |
| Benzoic Acid 100 | 5.0 | 100.0 | 20.0 | 100.0 |
| Creatine 100 | 5.0 | 100.0 | 20.0 | 100.0 |
| Creatinine 200 | 5.0 | 100.0 | 20.0 | 100.0 |
| Cysteine 100 | 5.1 | 102.0 | 20.3 | 101.5 |
| Cysteine Methyl Ester 100 | 5.1 | 102.0 | 20.2 | 101.0 |

TABLE-continued

| Other substances: (mg/dl) | Concentration of VC (mg/dl) | | | |
|---|---|---|---|---|
| | 5 | | 20 | |
| | Measured | Recovery (%) | Measured | Recovery (%) |
| Gentisic Acid | 100 | 5.1 | 102.0 | 20.0 | 100.0 |
| Glucose | 2000 | 5.0 | 100.0 | 20.0 | 100.0 |
| Glutathione (Reduced Form) | 100 | 5.0 | 100.0 | 20.0 | 100.0 |
| Potassium Oxalate | 100 | 5.0 | 100.0 | 20.0 | 100.0 |
| Pyruvic Acid | 20 | 5.1 | 102.0 | 20.1 | 100.5 |
| Salicylic Acid | 150 | 5.0 | 100.0 | 20.0 | 100.0 |
| Sodium Fluoride | 100 | 4.9 | 98.0 | 20.0 | 100.0 |
| Urea | 1000 | 4.9 | 98.0 | 20.0 | 100.0 |
| Uric Acid | 100 | 5.0 | 100.0 | 20.1 | 100.5 |

What is claimed is:

1. A composition for colorimetric analysis of ascorbic acid by the formation of colored complexes of a polyvalent metal ion in its lower valency which comprises: a complex of a chelating agent selected from the group consisting of ethylenediaminetetraacetic acid, trans-1,2-cyclohexanediamine-N,N,N',N'-tetraacetic acid, diethylenetriamine-N,N,N',N'',N'''-pentaacetic acid, triethylenetetramine-N,N,N',N''',N''''-hexaacetic acid and alkali metal salts thereof with a polyvalent metal ion in its higher valency; an indicator capable of reacting with said metal ion in its lower valency selected from the group consisting of o-phenanthroline, 4,7-diphenyl-1,10-phenanthroline 2,2'-bipyridine, cuproine, neocuproin and 2,2',2''-terpyridine; and a buffer capable of maintaining the pH value of the composition to from 3 to 6.5.

2. A composition as claimed in claim 1, wherein the polyvalent metal ion is one selected from the group consisting of iron, copper, cobalt and nickel ions.

3. A composition as claimed in claim 1, wherein said buffer is capable of maintaining the pH value of the composition from 4 to 6.

4. A method for colorimetric analysis of ascorbic acid which comprises contacting the composition of claim 1 or 2 with a solution containing ascorbic acid.

5. A method according to claim 4, wherein said solution is a body fluid.

6. A test strip for colorimetric analysis of ascorbic acid by the formation of colored complexes of a polyvalent metal ion in its lower valency, which comprises: a bibulous body retaining a complex of a chelating agent selected from the group consisting of ethylenediamine tetraacetic acid, trans-1,2-cyclohexanediamine-N,N,N',N'-tetraacetic acid, diethylenetriamine-N,N,N',N'',N'''-pentaacetic acid, triethylenetetramine-N,N,N',N''',N''''-hexaacetic acid and alkali metal salts thereof with a polyvalent metal ion in its higher valency; an indicator capable of reacting with said metal ion in its lower valency selected from the group consisting of o-phenanthroline, 4,7-diphenyl-1,10-phenanthroline, 2,2'-bipyridine, cuproine, neocuproine and 2,2',2''-terpyridine; a buffering agent; a dye for adjusting background color and a dispersing agent.

7. A test strip as claimed in claim 6, wherein the bibulous body is one selected from the group consisting of paper, filter paper, silica gel paper, DEAE cellulose paper, cloth, felt and a sintered porous body of glass or ceramic powder.

8. A test strip as claimed in claim 6, wherein the polyvalent metal ion is one selected from the group consisting of iron, copper, cobalt and nickel ions.

9. A test strip as claimed in claim 6, wherein the buffering agent is capable of maintaining pH value of the strip in wet state to from 3 to 6.5.

10. A test strip as claimed in claim 6, wherein the dispersing agent is one selected from the group consisting of polyvinylpyrrolidone, hydroxypropyl cellulose and polyethylene glycol.

11. A method for colorimetric analysis of ascorbic acid which comprises contacting the test strip of claim 6, 7, 8, 9 or 11 with a solution containing ascorbic acid.

12. A method according to claim 11, wherein said solution is a body fluid.

* * * * *